US006290923B1

United States Patent
Sollers et al.

(10) Patent No.: US 6,290,923 B1
(45) Date of Patent: Sep. 18, 2001

(54) STACK EMISSION CONTROL SYSTEM FOR REMOVING ORGANIC POLLUTANTS FROM AIR

(75) Inventors: Joseph S. Sollers, Lutherville; Roland N. Fracalossi; Walter V. V. Greenhouse, both of Baltimore; George J. Tolen, Ellicott City, all of MD (US)

(73) Assignee: Wm. T. Burnett & Co., Baltimore, MD (US)

(*) Notice: Subject to any disclaimer, the term of this patent is extended or adjusted under 35 U.S.C. 154(b) by 0 days.

(21) Appl. No.: 08/310,052

(22) Filed: Sep. 22, 1994

Related U.S. Application Data

(63) Continuation of application No. 08/007,816, filed on Jan. 22, 1993, now abandoned, which is a continuation of application No. 07/879,516, filed on May 4, 1992, now abandoned, which is a continuation of application No. 07/516,534, filed on Apr. 30, 1990, now abandoned.

(51) Int. Cl.[7] ........................................ B01J 8/00
(52) U.S. Cl. .......................................... 423/245.2
(58) Field of Search .................... 423/210, 236, 423/245.2; 55/233; 560/351

(56) References Cited

U.S. PATENT DOCUMENTS

| | | | |
|---|---|---|---|
| 1,046,212 | * | 12/1912 | Moscicki ............................. 55/233 |
| 2,560,635 | * | 7/1951 | Conyers ................................ 261/3 |
| 3,409,409 | * | 11/1968 | Sackett ............................... 55/233 |
| 3,959,451 | * | 5/1976 | Henderson et al. ................. 423/539 |
| 4,394,367 | * | 7/1983 | Foster ................................. 423/241 |
| 4,460,552 | * | 7/1984 | Zakrewski .......................... 423/210 |
| 4,552,667 | * | 11/1985 | Shultz ............................. 423/210.5 |
| 6,106,792 | * | 8/2000 | Griggs et al. ..................... 423/245.2 |

FOREIGN PATENT DOCUMENTS

| | | | |
|---|---|---|---|
| 2436781 | * | 2/1976 | (DE) . |
| 227052 | * | 9/1985 | (DE) ................................. 423/245.5 |
| 3631865 | * | 3/1988 | (DE) ................................... 423/242 |
| 1473815 | * | 4/1989 | (SU) ................................. 423/245.2 |

OTHER PUBLICATIONS

English–Language Translation of German Offenlegungsschrift 24 365 781 (Magerlein, Inventor), Published 2/76.*

* cited by examiner

Primary Examiner—Steven P. Griffin
(74) Attorney, Agent, or Firm—Breiner & Breiner, L.L.C.

(57) ABSTRACT

A stack emission control system utilized to remove organic contaminants as water-soluble solids from air collected from the vicinity of a polyurethane foam line assembly prior to the exhaust of the air into the surrounding atmosphere is described. A conventional packed tower scrubber is utilized containing an inert material as packing and pH-adjusted water as the wash fluid. The pH-adjusted water serves to remove essentially all of the organic contaminants as water-soluble solids from the air prior to exhaust of the air. The contaminant water-soluble solids are then readily separable from the pH-adjusted water by post-treatment to allow for the separate disposal of the essentially contaminant-free water and the contaminant solids.

12 Claims, 1 Drawing Sheet

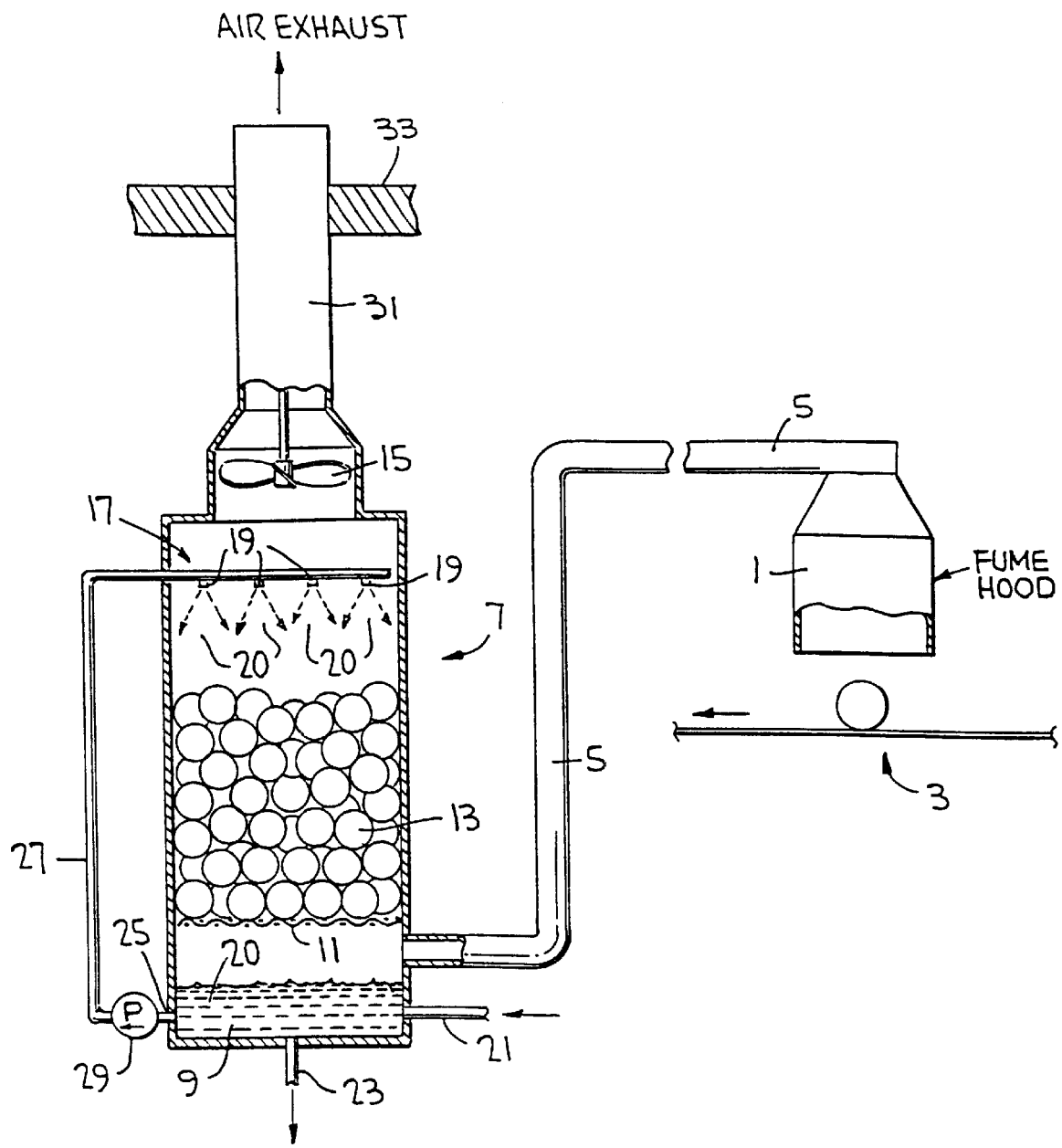

STACK EMISSION CONTROL SYSTEM FOR REMOVING ORGANIC POLLUTANTS FROM AIR

This is a continuation of application Ser. No. 8/007,816 filed on Jan. 22, 1993, now abandoned, which is a continuation of application Ser. No. 07/879,516 filed May 4, 1992, now abandoned, which is a continuation of application Ser. No. 07/516,534 filed Apr. 30, 1990, now abandoned.

FIELD OF THE INVENTION

The present invention is directed to a stack emission control system, preferably for use in removing organic pollutants from air present in polyurethane foam processing plants. More specifically, the stack emission control system includes a packed tower scrubber containing inert material as the packing and pH-adjusted water as the wash fluid. The pH-adjusted water serves to separate and remove the organic pollutants as water-soluble solids from the air prior to exhaust of the air from a plant into the surrounding atmosphere.

BACKGROUND OF THE INVENTION

It is known in the art to use a scrubber unit to remove impurities from air. It is recognized that the scrubber unit will contain a packing or filter material through which the polluted air will move and which is wet by a scrub or wash fluid. The type of filter and wash fluid used depends on the type of impurities which are to be separated and removed from the air. Generally, for effective removal of impurities from air, however, specific filter structures and/or specialty chemicals are required. Such filters normally require regeneration and use of specialty chemicals can result in high cost.

For example, U.S. Pat. No. 4,460,552 discloses a process for separating and removing impurities from air. The impurity-containing air is fed into a scrubber unit and passed through a filter material having an absorbent medium sprayed thereon. The filter pack is described as being one or more packs of stratified filter mats having a specified structure for removing the impurities from the air. The absorbent medium which is sprayed over the filter mats is stated to depend on the particular impurity to be removed, i.e., when an alkaline-reacting impurity is to be absorbed, an acidic absorbent is utilized and when an acid-reacting impurity is to be absorbed, an alkaline absorbent medium is utilized. If the impurity is soluble in water, acidic or alkaline-reacting aqueous solutions can be utilized in the filter process. In columns 6–7 of the patent, scrubber operations using the filter mats of the patent are compared with the operation of conventional packed columns, with each scrubber using the same absorbent medium. Improved results, as shown by the increased recovery over the conventional scrubbers, are attributed to the use of the specified filter mat structure.

U.S. Pat. No. 4,172,880 states that it is recognized in the art to remove pollutants from the air prior to exhaust of the air from an industrial production area through the use of a scrubbing tower. A scrubbing tower suitable for use includes inert material as packing which is wet by a downward spray of fluid. The patent states that in the metal casing industry where the air contains contaminants such as triethylamine, dimethylethylamine, ammonia, or the like, in trace quantities that an acid solution can be used as a scrubbing liquid.

U.S. Pat. No. 2,560,635 discloses a scrubbing apparatus wherein a gas passes upward through a scrubbing or baffle means, such as touching balls. A wash fluid flows downward over the baffle means from a spray outlet positioned above the baffle means as the gas flows upward through the baffle means. The wash fluid utilized can be water alone, an aqueous solution, or any other suitable fluid. The only specific gas referred to for removal is $S_2$ which when contacted with wash water is changed to $H_2SO_3$.

Accordingly, the art does not disclose the use of a pH-adjusted water as a wash fluid in a packed scrubber unit utilizing only an inert material as packing to remove essentially all of the organic impurities from air present in foam processing plants where the organics to be removed include toluene diisocyanate (TDI). More particularly, the art does not disclose the removal of one or more organic pollutants, which are neither acid nor basic, from air as water-soluble solids using a pH-adjusted wash water with only inert packing. Even more specifically, the removal of toluene diisocyanate from air utilizing acidic water is not taught in the art.

OBJECTS OF THE INVENTION

A primary object of the present invention is to provide for the removal as water-soluble solids of organic pollutants or impurities from air present in polyurethane foam processing plants utilizing pH-adjusted water as a wash fluid in a packed tower scrubber utilizing only inert packing material, particularly where the organic pollutants are neither acidic nor basic in nature, resulting in substantially contaminant-free air.

A further primary object of the present invention is to provide for the removal as water-soluble solids of organic impurities which are neither acidic nor basic from air utilizing water as a wash fluid in a packed tower scrubber wherein the pH of the water has been adjusted so that the water is either alkaline or acidic, and preferably is acidic, resulting in substantially contaminant-free air.

A further primary object of the present invention is to provide for the removal, as a water-soluble solid, of toluene diisocyanate from air prior to exhaust of the air into the surrounding atmosphere through the use of acidic water as a wash fluid in a packed tower scrubber which utilizes only an inert packing material and which results in substantially contaminant-free air.

BRIEF DESCRIPTION OF THE INVENTION

The present invention is directed to a stack emission control system for removing organic pollutants or impurities as water-soluble solids from air, which enter the air from a polyurethane foam processing operation, prior to exhaust of the air into the surrounding atmosphere. In particular, the emission control system is useful in processing lines which involve the thermal treatment of polyurethane foam, since there is the possibility of generating organic pollutants, such as toluene diisocyanate, upon the thermal decomposition of foam, such as polyether or polyester based polyurethane foams. It is desirable to remove the organic pollutants from the work area and to prevent their discharge into the surrounding atmosphere.

To remove organic pollutant-containing air from the vicinity of a foam processing line which can be either a line where the polyurethane foam is initially manufactured or where the finished polyurethane foam is subsequently treated, for example, laminated by heat treatment to textile. a canopy-type fume hood is positioned in relation to the processing line so that the hood can be utilized to take up the air containing the organic pollutants, such as toluene diisocyanate, from the line area. A duct is connected to the hood and serves as a means of conveying the impure air to a packed scrubber unit.

The scrubber apparatus can be of a conventional packed tower scrubber structure. A suitable scrubber unit contains a wash fluid reservoir in the base of the unit. The air conveyed to the scrubber is received into the scrubber unit through the duct which is connected to the scrubber unit at a point just above the wash fluid reservoir in the base of the scrubber unit. The scrubber unit has a packed column of inert packing material, such as balls or the like, to provide a torturous path through which the air will travel as the air passes upward through the scrubber unit. A pH-adjusted water wash fluid is sprayed down from one or more sprayheads which are positioned over the packing through which the air is moving. The water has had its pH adjusted so that the water has either an alkaline or acidic pH. The addition of an acid compound in a quantity sufficient to give the water an acidic pH is highly preferred and has been found to provide surprising results in the substantial complete removal of toluene diisocyanate (TDI) from air. The acidic water reacts with the substantial portion of TDI, which is the major organic contaminant present upon the thermal decomposition of polyether or polyester based polyurethane foam. The pH-adjusted water serves to separate and remove the impurities, i.e., TDI and toluene diamine (TDA) from the air as water-soluble solids. The contaminant-free air is then drawn out of the scrubber unit into an exhaust conduit through the use of an exhaust fan. The air is then expelled from the plant through the exhaust conduit into the surrounding atmosphere.

The pH-adjusted water sprayed down over the inert packing and the contaminants in the form of water-soluble solids are collected in the fluid reservoir in the base of the scrubber unit. This water can be recirculated for use in the sprayheads positioned over the packing by a water pump. The pH of the wash fluid is monitored so that it can be maintained in the range of the desired pH.

The process of the invention serves to remove essentially all of the organic impurities as water-soluble solids and collect them in the reservoir unit. These water-soluble solids are readily removable from the wash water by post treatment such as distillation or the like so as to leave essentially contaminant-free wash water. Alternatively, the wash water with the impurities can be disposed of through a sewer system, or the like, since the water-solubles have been converted to non-hazardous materials. TDI is, therefore, removed from the air utilizing conventional scrubbing equipment and pH-adjusted water. Accordingly, the process is efficient and economic in that it avoids the use of specialty chemicals or a filter which must be regenerated or otherwise treated in order to operate effectively over a continuous period of time.

BRIEF DESCRIPTION OF THE DRAWING

The sole FIGURE is a schematic representation of the apparatus utilized in the process of the present invention, i.e., a canopy-type fume hood positioned in relation to a polyurethane foam processing line, a connecting conduit, a scrubber unit including a column of inert packing material, sprayheads, wash fluid reservoir, and the like.

DESCRIPTION OF THE PRESENTLY PREFERRED EMBODIMENT

The present invention is useful for controlling the emission of pollutant-containing air or smoke from a manufacturing or treatment process, in particular a polyurethane foam processing operation, through the use of a packed tower scrubber utilizing only pH-adjusted water as a wash fluid and inert material as packing. One process in which the scrubber unit of the present invention can be utilized is in the manufacture of polyurethane foam products, in particular polyester or polyether-based polyurethane flexible or rigid foams, which is an exothermic reaction. Another important process is where a polyurethane foam is laminated to a textile(s) where thermal treatment of the foam is involved.

When polyether or polyester based flexible or rigid polyurethane foams are subjected to thermal conditions, some decomposition of the foam results. The extent of decomposition depends upon the degree of heat present and the length of time the foam is exposed to the heat. Upon thermal decomposition, a volatile yellow smoke is released from the polyether or polyester based polyurethane foam. It is recognized in the art, as in the article entitled "Nitrogen-containing Products from the Thermal Decomposition of Flexible Polyurethane Foams" by Woolley, *Br. Polym. J.*, Vol. 4, pp. 27–43 (1972), that the yellow smoke released contains toluene diisocyanate (TDI). TDI is neither acidic nor basic in nature. In most foam treatment processes, TDI is only released in trace quantities due to the minimal exposure of the foam to thermal decomposition. However, in view of the health and environmental concerns, it is desirable to remove the organic impurities released into the air from the air before the air is dissipated into the surrounding atmosphere.

One foam treatment process with which the present invention is suitable for use, and with which the present invention will be described, is a polyurethane foam lamination process. In such a process, polyurethane foam is softened using a gas flame so that the foam can be laminated on one or more sides to another material, such as a polyethylene film or a cloth-like material. Even though the flame is only in contact with the foam instantaneously, there is the possibility for TDI to be generated due to thermal decomposition of the polyurethane foam and, accordingly, trace amounts of TDI are emitted into the air. With reference to the drawing, a conventional canopy-type fume hood 1 is positioned over a lamination line 3 so that the organic impurity-containing air, in particular TDI-containing air, is effectively captured and taken up by the fume hood. The captured air then passes through a connecting duct or conduit 5 to a scrubber unit denoted generally as 7.

The scrubber unit is basic in structure and does not require the use of specialty chemicals as a wash fluid or specialized packing or filter materials. The scrubber unit useful in the present invention need only utilize an inert material as packing.

More particularly, scrubber unit 7 contains a wash fluid reservoir 9 in the base of the scrubber unit, or optionally located outside the scrubber unit. Conduit 5, through which the contaminated air passes to the scrubber unit, is connected to the unit above the fluid level in the wash fluid reservoir 9 and below perforated structure 11 also positioned in the scrubber unit. Perforated structure 11 can be a screen mesh, grating or other grate-like structure. Perforated structure 11 is utilized to hold packing 13 in place in the upper portion or column of scrubber unit 7 while allowing fluid to pass through the structure. Structure 11 will be made of a material having a strength suitable for its purpose.

Packing 13 can be any suitable inert material shaped to give maximum surface area and air/wash fluid contact. Such devices are known in the art. The shaped nature of the inert material is desired to be such which provides a torturous path through which the air received into the scrubber unit will travel. An exhaust fan 15 is positioned above the packing in the scrubber unit and serves to pull the air upward through the scrubber unit. Positioned above the inert packing material 13 and below exhaust fan 15 is a spray apparatus 17. Spray apparatus 17 can contain one or more sprayheads 19. The sprayheads serve to spray a wash fluid 20 over the inert material in the scrubber unit as the impurity-containing air moves upward through the inert material. As the wash fluid flows downward through the inert material, it will contact the impurities contained in the air and eventually pass through perforated structure 11 and into fluid reservoir 9. The wash water will remain in the reservoir until taken up for reuse or discharge. The solids are generally in the form of a water-soluble salt. The water-soluble salts can be removed from the wash water by post-treatment such as distillation. Since the level of water-soluble solids is low, it is often possible to discharge the wash water directly into a sewer system.

The fluid reservoir has a fluid inlet 21 for initially filling and replenishing, when necessary, the reservoir with wash fluid. The reservoir additionally has an outlet 23 for when the reservoir is to be emptied. Further, the reservoir contains an opening 25 which is connected to conduit 27 so that the wash fluid can be recirculated from reservoir 9 for reuse through sprayheads 19. A pump 29 is connected to conduit 27 for pumping wash fluid 20 from reservoir 9 to sprayheads 19.

The organic impurities present in the air are removed therefrom as water-soluble salts or solids through the use of the wash fluid. Contact between the wash fluid and the impurities in the air is enhanced by the movement of the air and wash fluid through the packed column as will be further described below. Once the air has moved pass the packing, the impurities have been essentially all removed from the air and the air is drawn upward by exhaust fan 15 into the air exhaust conduit 31 where it then passes into the atmosphere. Exhaust conduit 31 passes through a building roof 33 or the like into the outside surrounding atmosphere.

At the time the air is taken up by fume hood 1, the emission is discolored due to the impurities contained therein. By the time the air is emitted through air exhaust conduit 31, the emission is perfectly clear. Substantially all of the organic contaminants, in particular TDI, contained in the air is removed. The manner of removal of the impurity involves the use of pH-adjusted water as the wash fluid in the scrubber unit.

More specifically, an inorganic or organic acid, or an inorganic or organic alkaline material is added to the water until the desired acidic or alkaline pH is reached. Suitable acids for addition to the wash water include sulfuric acid, hydrochloric acid, phosphoric acid, or the like. When utilizing an acid, the water pH is preferably adjusted to a pH in the range of from about 6 to 1, and most preferably to a pH of from 4 to 6. Suitable alkaline materials which can be added to the wash water include the amines, sodium or potassium hydroxide, ammonia, or the like. When adding an alkaline material, the pH of the water preferably is adjusted to be within the range of from about 8 to 12, and most preferably to a pH of from 8 to 9.

The use of pH-adjusted water to remove an impurity which is neither acidic or basic for substantially complete removal of the impurity is surprising, in particular when using acidic water. Thus, the substantial complete removal of TDI from air as emitted from a foam lamination process is surprising in that it would not be expected that acidic water would provide the advantage of removing substantially all the TDI as a water-soluble solid from the TDI-containing air since TDI is neither acidic nor basic. It is further surprising since it is known that water alone reacts with TDI to convert TDI to toluene diamine (TDA). However, in the past, TDI has not been sufficiently removed from TDI-contaminated air utilizing water alone as the wash water and, therefore, expensive or time consuming filtering materials were utilized as the packing in conjunction with the wash water which necessarily increased the cost of the operation. Such packing as previously used additionally required periodic regeneration in order to remain effective, and accordingly, resulted in added expense and time. The present invention only requires the use of an inert packing material. The packing is used to provide a high surface area through which the impurity-containing air will travel so that the air has sufficient opportunity to come into contact with the wash fluid. The inert material is preferably shaped material, such as balls, to provide a torturous path through which the air can travel. This provides more opportunity for the wash fluid to contact the impurities.

Virtually all organic pollutants from the collected air are converted to water-soluble solids by the scrubber unit and are, in turn, separated from the scrubber wash water by post-treatment, if desired, prior to discharge of the water. Due to the water-soluble solid nature of the collected contaminants, the contaminants are readily removable, i.e., separable from the water by distillation or other post-treatment processes. Accordingly, when the water is discharged from the scrubber reservoir, the water will contain the water-soluble contaminants. These organics are non-reactive, salt-type materials. The air discharged into the atmosphere will contain less than about 1 part per million (ppm) organics, such as TDI. The air discharged will be colorless, with substantial odor reduction.

With regard to the use of alkaline pH-adjusted water, the scrubber functions in the same manner.

In test runs conducted using the process of the present invention, organic contaminant-containing air was taken up from the vicinity of a laminating process involving polyether polyurethane foam. A gas flame was used to soften the polyurethane foam in such a manner that the foam could be laminated on one side to a polyethylene film and on the opposite side to a cloth-like material. The contaminant-containing air was taken up by a fume hood and fed into a scrubber unit as described above. Acidic water having a pH of from 3 to 6 was utilized as the wash fluid. Stack emission samples were taken to test for TDI, hydrogen cyanide (HCN), and carbon monoxide (CO). The test samples regarding TDI emission will be described first.

Stack samples were collected and analyzed for TDI emissions by pumping air through spill-proof impingers which contained an absorber solution. The impinger sampling procedure involved bubbling air at approximately one liter per minute through a solution of 2.2 by $10^{-4}$ M p-nitrobenzyl propylamine (nitro reagent) which converts isocyanate to stable urea derivatives. The urea derivatives are identified by HPLC to analytically measure TDI. Air flow for the stack was measured by using a pitot tube which is a standard device for measuring velocity pressure (and hence velocity) in ducts. A pitot traverse, which involves measuring the velocity at a number of points across the duct area, was taken by using five sampling ports located in the duct on top of the roof. By knowing the amount of TDI emitted and the total volume of air being exhausted, the total volume of TDI emissions per hour can be calculated. Three sets of impinger samples were collected simultaneously while laminating flexible polyurethane foam. The collection efficiency for the first impinger was greater than 96%. The isomers for TDI can be quantitatively identified by HPLC. The two isomers of TDI and the total TDI are reported in parts per billion (ppb). Only the total TDI concentration was used to calculate the emission rate in pounds per hour. The results are calculated as maximum TDI emissions only while foam was being laminated. Foam was laminated for approximately 20 minutes per hour or for approximately 2.67 hours per 8 hour work day. Additionally, two impingers were used in series for each sampling. For each set of samples, the "F" following the number indicates the front impinger and "B" indicates the back up impinger. The test results are shown in Table I below.

and $$lbs/ft^3 = mg/liter \times 6.24 \times 10^{(-5)} \text{ with } mg/liter = \frac{\mu g \text{ TDI Measured} \times 0.001}{\text{liters of air sampled}}$$

and (3) the abbreviation "N.D." refers to non-detectable and is less than the limit of quantitation of $1.0 \mu g$ TDI/sample for each isomer.

The stack emissions were also tested for carbon monoxide and hydrogen cyanide. As with the TDI samples, the samples were collected from the foam laminating oven stack. All the samples were collected during normal operating conditions.

TABLE I

Toluene Diisocyanate Stack Emissions

| Sample No. | Production Run Period | Sampling Port | Polyurethane Foam Type | Volume Liters | TDI Concentration, ppb | | | Total $\mu g$ | TDI Emissions lbs./hr. |
|---|---|---|---|---|---|---|---|---|---|
| | | | | | 2,4-Isomer | 2,6-Isomer | Total | | |
| 1F | 8:50–9.48 (19.89 min) | 3 | Foam A Polyether | 19.89 | 487.5 | 303.8 | 791.1 | 112 | 0.214 |
| 1B | 8:50–9.48 (19.89 min) | | | | 7.8 | 7.1 | 14.8 | 2.1 | |
| 2F | 8:50–9.48 (19.89 min) | 5 | | 21.08 | 551.5 | 290.0 | 841.5 | 126.24 | 0.226 |
| 2B | 8:50–9.48 (19.89 min) | | | | 8.4 | N.D. | 8.4 | 1.26 | |
| 3F | 8:50–9.48 (19.89 min) | 1 | | 21.08 | 554.5 | 296.4 | 850.8 | 127.64 | 0.231 |
| 3B | 8:50–9.48 (19.89 min) | | | | 10.8 | 7.3 | 18.1 | 2.72 | |
| 4F | 10:19–11:10 (16.08 min) | 3 | Foam B Polyether | 16.08 | 515.6 | 375.8 | 891.3 | 102 | 0.240 |
| 4B | 10:19–11:10 (16.08 min) | | | | 5.2 | 6.1 | 11.4 | 1.3 | |
| 5F | 10:19–11:10 (16.08 min) | 5 | | 17.04 | 609.1 | 382.5 | 991.5 | 120.24 | 0.269 |
| 5B | 10:19–11:10 (16.08 min) | | | | 10.2 | 8.2 | 18.5 | 2.24 | |
| 6F | 10:19–11:10 (16.08 min) | 1 | | 17.04 | 577.1 | 359.2 | 936.3 | 113.54 | 0.249 |
| 6B | 10:19–11:10 (16.08 min) | | | | N.D. | N.D. | N.D. | <1.00 | |
| 7F | 11:45–12:50 (18.05 min) | 3 | Foam C Polyether & F.R. | 18.05 | 1167.7 | 544.9 | 1712.7 | 220 | 0.476 |
| 7B | 11:45–12:50 (18.05 min) | | | | 50.6 | 25.7 | 76.3 | 9.8 | |
| 8F | 11:45–12:50 (18.05 min) | 5 | | 19.13 | 1360.2 | 567.1 | 1927.3 | 262.38 | 0.531 |
| 8B | 11:45–12:50 (18.05 min) | | | | 49.7 | 20.0 | 69.6 | 9.48 | |
| 9F | 11:45–12:50 (18.05 min) | 1 | | 19.13 | 1245.9 | 522.6 | 1768.5 | 240.76 | 0.490 |
| 9B | 11:45–12:50 (18.05 min) | | | | 54.1 | 21.2 | 75.2 | 10.24 | |

With regard to Table I, it is noted that (1) in the production run period, the time refers to the actual time that foam was being laminated during the production run; (2) that the pounds per hour referred to under the TDI Emissions was based on the following:

$$lbs/hr = Q.ft^3/min. \times lbs/ft^3 \text{ TDI} \times 60 \text{ min./hr.}$$

where $Q$=volumetric air flow in stack=9984 $ft^3$/min. (ACFM)

The sampling for carbon monoxide was conducted using Drager tube, part no. 6733051. The measurement range of the tubes is 2–300 parts per million (ppm). If ten strokes are taken on the Drager Gas Detector Pump Model 31, the range of the tube is 2–60 ppm. A total of ten strokes were taken for all carbon monoxide testing. The tubes were inserted well into the stack using a support rod. The results were consistent from sample to sample and for each of the three materials tested.

Sampling for hydrogen cyanide was conducted using Drager tubes, part no. CH25701 and the bubbler method as outlined in "The State Of Tennessee Occupational, Safety, and Health Agency (TOSHA) Industrial Hygiene Technical Manual." The Drager tubes had a measurement range of 2–150 ppm. With five pump strokes, the measurement range was 2–30 ppm. A total of five strokes was used for all hydrogen cyanide Drager tube sampling. As with the carbon monoxide testing, the tubes were inserted well into the stack using a rigid support rod. The results were consistent from sample to sample and for each of the three materials tested.

The bubbler samples were taken with a Gilian constant flow pump. The pre- and post-flow calibrations were accomplished with a Gilian Primary Reference Flow Meter. The flow was set at approximately 1,000 ml per minute. A 37 mm 0.8 micron mix cellulose ester filter was inserted into the stack to catch the particulate cyanide sample. The gaseous sample was passed through a FEP teflon line to the 10 ml 0.1 N sodium hydroxide impinger where the hydrogen cyanide was collected.

The sample times varied between 15 and 19 minutes. The average run time per roll of foam was 2.5–3 minutes.

The results are set forth below in Table II.

TABLE II

| A. Stack Data (Average) | | |
| --- | --- | --- |
| Flow (ACFM) | | 9,994 |
| Flow (DSCFM) | | 9,166 |
| Stack Temperature (° F.) | | 92 |
| Stack Size (inches) | | 35 × 35 |
| Sample | Foam A Polyether | Foam B Polyether | Foam C Polyether & F.R. |
| B. Carbon Monoxide - Drager Tubes | | | |
| 1 | 25 ppm | 20 ppm | 20 ppm |
| 2 | 25 ppm | 22 ppm | 20 ppm |
| C. Hydrogen Cyanide - Drager Tubes | | | |
| 1 | 6 ppm | 6 ppm | 6 ppm |
| 2 | 6 ppm | 6 ppm | 6 ppm |
| D. Hydrogen Cyanide - Bubbler Method | | | |
| 1 | 3.7 mg/m$^3$ | 3.8 mg/m$^3$ | 5.4 mg/m$^3$ |

As will be apparent to one skilled in the art, various modifications can be made within the scope of the aforesaid description. Such modifications being within the ability of one skilled in the art form a part of the present invention and are embraced by the appended claims.

It is claimed:

1. A process of separating and removing organic contaminants as water-soluble solids from air, wherein the contaminant-containing air is taken up from the immediate environment of a polyurethane foam processing line comprising passing the organic contaminant-containing air through a packed tower scrubber in the absence of an active filter material and the presence of an inert material present in said tower as packing in such a manner as to provide a plurality of tortuous channels through the packed tower, and simultaneously therewith spraying pH-adjusted water as a wash fluid down over the packing as the air passes through the packing so that each of the organic contaminant-containing air and wash fluid are caused to move through the plurality of tortuous channels in the packing so as to cause the pH-adjusted water to come into contact with the organic contaminants in the air, thereby removing the contaminants from the air as water-soluble solids.

2. The process according to claim 1 wherein said organic contaminants are neither acidic nor basic in nature.

3. The process according to claim 1 wherein said pH-adjusted water has its pH adjusted by the addition of an acid compound to water until the pH of said water is within a range of from 2 to 6.

4. The process according to claim 1 wherein said pH-adjusted water has its pH adjusted by the addition of an alkaline compound to water until the pH of said water is within the range of from 8 to 12.

5. The process according to claim 3 wherein said acid compound is selected from the group consisting of sulfuric acid, phosphoric acid and hydrochloric acid.

6. The process according to claim 4 wherein said alkaline compound is selected from the group consisting of amines, sodium or potassium hydroxide and ammonia.

7. The process according to any one of claims 1–6 wherein the organic contaminant includes toluene diisocyanate, and said TDI is reduced to a level of less than 1 ppm.

8. A process of separating and removing an organic diisocyanate as a water-soluble salt from air taken up from the immediate environment of a polyurethane foam processing line comprising passing toluene diisocyanate-containing air through a packed tower scrubber in the absence of an active filter material and the presence of inert packing present in said tower in such a manner as to provide a plurality of tortuous channels through the packed tower such that said toluene diisocyanate-containing air passes through said channels present in said packing, and simultaneously therewith spraying acidic water as a wash fluid over the packing within the scrubber, whereby as said toluene diisocyanate-containing air passes through said channels formed by said inert packing of said scrubber which is being wet with said acidic water, said air contacts said acidic water such that said toluene diisocyanate is separated and removed from said air as a water-soluble salt, said toluene diisocyanate being reduced to a level of less than 1 ppm.

9. A process of removing toluene diisocyanate-containing air from a polyurethane foam processing line and thereafter separating said toluene diisocyanate as a water-soluble solid from the air comprising:

(a) uptaking toluene diisocyanate-containing air from a foam processing line by a fume hood;

(b) conveying said toluene diisocyanate-containing air to a scrubber unit having a packed column having tortuous channels therethrough and a wash fluid sprayed over said packed column such that said wash fluid flows through said channels, wherein said wash water is acidic water and said packed column contains an inert material and does not contain an active filter material;

(c) causing said toluene diisocyanate-containing air to move upward through said channels in said packed column of said scrubber unit so as to come into contact with said acidic water in said packed column whereby said toluene diisocyanate is separated as a water-soluble solid from said air by said acidic water and removed from said air by said acidic water;

(d) causing said air to be exhausted from said scrubber unit and emitted into the atmosphere; and (e) separating said toluene diisocyanate water-soluble solid from said wash water by post-treatment to provide wash water essentially free from toluene diisocyanate.

10. The process according to claim 8 or claim 9 wherein said acidic water includes an acid selected from the group consisting of phosphoric acid, hydrochloric acid, sulfuric acid, and acetic acid.

11. The process according to claim 8 or claim 9 wherein said acidic water has a pH in the range of from 2 to 6.

12. The process according to claim 8 or claim 9 wherein said acidic water includes an acid present in an amount sufficient to bring the pH of said water to a pH within the range of from about 2 to 6.

* * * * *